US012629043B2

(12) United States Patent
    Liu

(10) Patent No.: US 12,629,043 B2
(45) Date of Patent: May 19, 2026

(54) WEARABLE DEVICE AND WEARING STATUS DETECTION METHOD

(71) Applicant: Huawei Technologies Co., Ltd., Shenzhen (CN)

(72) Inventor: Xuelian Liu, Xi'an (CN)

(73) Assignee: HUAWEI TECHNOLOGIES CO., LTD., Shenzhen (CN)

( * ) Notice: Subject to any disclaimer, the term of this patent is extended or adjusted under 35 U.S.C. 154(b) by 334 days.

(21) Appl. No.: 18/264,132

(22) PCT Filed: Jan. 21, 2022

(86) PCT No.: PCT/CN2022/073187
    § 371 (c)(1),
    (2) Date: Aug. 3, 2023

(87) PCT Pub. No.: WO2022/166617
    PCT Pub. Date: Aug. 11, 2022

(65) Prior Publication Data
    US 2024/0090784 A1      Mar. 21, 2024

(30) Foreign Application Priority Data
    Feb. 4, 2021    (CN) .......................... 202110156315.5

(51) Int. Cl.
    *A61B 5/024* (2006.01)
    *A61B 5/00* (2006.01)
    (Continued)

(52) U.S. Cl.
    CPC ........ *A61B 5/02438* (2013.01); *A61B 5/0017* (2013.01); *A61B 5/02433* (2013.01);
    (Continued)

(58) Field of Classification Search
    CPC .............. A61B 5/02438; A61B 5/0017; A61B 5/02433; A61B 5/681; A61B 5/021;
    (Continued)

(56) References Cited

U.S. PATENT DOCUMENTS 10,874,348 B1 * 12/2020 Han ..................... A61B 5/6843
12,089,931 B1 * 9/2024 Duan ................... A61B 5/6844
(Continued)

FOREIGN PATENT DOCUMENTS

CN        109875572 A      6/2019
CN        111134648 A      5/2020
WO        2020088639 A1    5/2020

*Primary Examiner* — Abid A Mustansir
(74) *Attorney, Agent, or Firm* — Conley Rose, P.C.

(57)                    ABSTRACT
A wearable device includes a first optical transmitter configured to transmit first optical signals. One or more first optical sensors are configured to detect the first optical signals. A second optical transmitter, in the form of a vertical-cavity surface-emitting laser, is configured to transmit laser light. One or more second optical sensors are configured to detect the laser light transmitted by the second optical transmitter. One or more processors, connected to the first optical transmitter, the first optical sensors, the second optical transmitter, and the second optical sensors, and are configured to determine a wearing status of the wearable device based on optical signals detected by the first optical sensors and the second optical sensors.

20 Claims, 9 Drawing Sheets

(51) Int. Cl.
    *G04G 17/04*         (2006.01)
    *G04G 21/02*         (2010.01)

(52) U.S. Cl.
    CPC ............. *A61B 5/681* (2013.01); *G04G 17/04*
               (2013.01); *G04G 21/025* (2013.01)

(58) Field of Classification Search
    CPC ............ A61B 5/02416; A61B 5/14542; A61B
               5/14551; A61B 5/6844; A61B 5/318;
          A61B 5/332; A61B 5/0205; G04G 17/04;
                                 G04G 21/025
    See application file for complete search history.

(56)                   References Cited

U.S. PATENT DOCUMENTS

| | | | |
|---|---|---|---|
| 2015/0366507 A1* | 12/2015 | Blank ................. | A61B 5/6826 |
| | | | 600/323 |
| 2016/0007925 A1* | 1/2016 | Mirov ................. | A61B 5/0059 |
| | | | 356/400 |
| 2017/0020399 A1 | 1/2017 | Shemesh et al. | |
| 2018/0114875 A1 | 4/2018 | Ho et al. | |
| 2020/0367827 A1 | 11/2020 | Min et al. | |
| 2022/0022814 A1 | 1/2022 | Xi et al. | |

\* cited by examiner

A-A

WEARABLE DEVICE AND WEARING STATUS DETECTION METHOD

This application claims priority to Chinese Patent Application No. 202110156315.5, filed with the China National Intellectual Property Administration on Feb. 4, 2021 and entitled "WEARABLE DEVICE AND WEARING STATUS DETECTION METHOD", which is incorporated herein by reference in its entirety.

TECHNICAL FIELD

This application relates to the field of electronic device technologies, and in particular, to a wearable device supporting wearing detection.

BACKGROUND

At present, lots of wearable devices have a wearing detection function. There are mainly two manners of wearing detection of the wearable devices. One is to perform wearing detection by using an infrared (Infrared, IR) light source and a photodiode (Photodiode, PD) module that are used for heart rate measurement. The other is to implement wearing detection by further using a capacitive sensor based on the IR light source and the PD module that are used in the first manner. When the wearing detection function is implemented by using the IR light source and the PD module that are used for heart rate measurement, textures cannot be accurately distinguished in a non-worn state, and a wearing status is falsely determined in a loosely-worn state. This is a key factor affecting user experience. Although the capacitive sensor is further used to implement the wearing detection function with effectively improved accuracy of texture differentiation in the non-worn state, for some textures with a dielectric constant that is close to that of a human body and the loosely-worn state, wearing experience is not considerably enhanced. In addition, as a wearable device has a small volume, a space for stacking is limited, and the capacitive sensor is easily affected by parasitic capacitance. All factors mentioned above are key factors affecting user experience.

As users have increasingly higher requirements on experience of measuring a heart rate and a blood pressure, having an electrocardiogram, and the like on a wearable device, a wearing detection solution featuring low power consumption and high reliability increasingly becomes a main requirement of the users.

SUMMARY

Embodiments of this application provide a wearable device and a wearing status detection method, to effectively detect a wearing status of the wearable device and improve accuracy of measuring physiological data, for example, a heart rate, without considerably increasing power consumption of a system.

To achieve the objectives, the following technical solutions are used in implementations of this application.

A first aspect provides a wearable device, including: a first optical transmitter, configured to transmit at least one color of light; first optical sensors, configured to receive the at least one color of light; a second optical transmitter, where the second optical transmitter may be a vertical-cavity surface-emitting laser (VCSEL), that is, a light-emitting element, and is configured to transmit laser light; second optical sensors, configured to detect the laser light transmitted by the second optical transmitter; and a processor, connected to the first optical transmitter, the first optical sensors, the second optical transmitter, and the second optical sensors, and configured to determine a wearing status of the wearable device based on optical signals detected by the first optical sensors and the second optical sensors. The wearing status indicates whether a user has worn the wearable device and tightness of wearing, to solve existing problems such as a high false identification rate with a loosely-worn state, a proneness of capacitance to be affected by an environment, and a high power consumption, so that experience in measurement of physiological data, for example, a heart rate, a blood pressure, and an electrocardiogram performed by the wearable device can be further optimized with improved accuracy of the measurement.

In an optional embodiment, the wearable device includes at least one second optical transmitter and at least four second optical sensors, the at least four second optical sensors are evenly disposed around the second optical transmitter, and the second optical sensors are disposed between the second optical transmitter and the first optical sensors. The at least four second optical sensors are evenly disposed around the second optical transmitter, so that laser light detection in at least four directions of up, down, left, and right can be covered, to improve accuracy of wearing status detection.

In an optional embodiment, the wearable device includes four first optical sensors, and the four first optical sensors are disposed in a one-to-one correspondence with four of the at least four second optical sensors. With the disposition, laser light leaked in the four directions of up, down, left, and right can be detected, to determine a direction in which wearing is loose, and improve accuracy of wearing status detection.

In an optional embodiment, the wearable device includes eight first optical sensors and four second optical sensors, the first optical sensors are evenly disposed around the second optical transmitter and the second optical sensors, and four of the eight first optical sensors are disposed in a one-to-one correspondence with the four second optical sensors. With the disposition, laser light leaked in eight directions can be detected with more comprehensiveness, to accurately detect tightness of wearing, and improve accuracy of wearing status detection.

In an optional embodiment, when a quantity of first optical sensors that have received the laser light is 0, and a quantity of second optical sensors that have received the laser light is greater than or equal to 1, the processor determines that the wearing status of the wearable device is comfortably-worn; or when a quantity of first optical sensors that have received the laser light is greater than or equal to 1, and a quantity of second optical sensors that have received the laser light is greater than or equal to 1, the processor determines that the wearing status of the wearable device is loosely-worn.

In an optional embodiment, when a quantity of first optical sensors that have received the laser light is 0, and a quantity of second optical sensors that have received the laser light is greater than or equal to 2, the processor determines that the wearing status of the wearable device is comfortably-worn; or when a quantity of first optical sensors that have received the laser light is greater than or equal to 1, and a quantity of second optical sensors that have received the laser light is greater than or equal to 1, the processor determines that the wearing status of the wearable device is loosely-worn.

In an optional embodiment, the wearable device further includes a display screen, configured to display the wearing status determined by the processor, so that the user can view and learn about the wearing status of the wearable device conveniently.

In an optional embodiment, the wearable device further includes a prompt component, configured to prompt the user when the wearing status of the wearable device is loosely-worn.

In an optional embodiment, the wearable device includes a capacitive sensor, where the capacitive sensor is configured to: detect contact capacitance, and transmit a detected capacitance value to the processor; and the processor determines the wearing status of the wearable device based on the optical signals detected by the first optical sensors and the second optical sensors and the capacitance value. By further using the capacitive sensor, whether the user has worn the wearable device is first detected, and then the VCSEL is used to detect tightness of wearing after the wearable device is worn, to enable VCSEL reflection feature detection mainly in a loosely-worn scenario. In this way, power consumption of a system is not considerably increased.

In an optional embodiment, the first optical transmitter is configured to transmit infrared light; the first optical sensors are configured to: detect the infrared light that is reflected, and transmit a detected infrared light signal to the processor; and the processor determines the wearing status of the wearable device based on the laser signals detected by the first optical sensors and the second optical sensors, the infrared light signal detected by the first optical sensors, and the capacitance value. Based on an IR reflection feature, whether the user has worn the wearable device is first detected, and then a VCSEL is used to detect tightness of wearing after the wearable device is worn. VCSEL reflection feature detection is enabled mainly in a loosely-worn scenario, and in this way, power consumption of a system is not considerably increased.

In an optional embodiment, an optical transmitter and an optical sensor in a PPG module are used as the first optical transmitter and the first optical sensors, and the second optical transmitter is in a center of the PPG module. Light is transmitted and detected by using the existing PPG module, so that manufacturing costs can be reduced and a space for stacking can be saved.

In an optional embodiment, a shading wall is disposed between the first optical transmitter and the first optical sensors, between the second optical transmitter and the second optical transmitter, and/or between the second optical sensors and the first optical transmitter, to prevent light leakage, and avoid mutual interference of light rays.

A second aspect provides a wearing status detection method. The method is applied to the wearable device according to the first aspect, and the method includes: A second optical transmitter transmits laser light, where the second optical transmitter is a vertical-cavity surface-emitting laser, that is, a light-emitting element; first optical sensors and second optical sensors detect the laser light that is reflected; and the wearing status of the wearable device is determined based on laser signals detected by the first optical sensors and the second optical sensors. A generated light current in the first optical sensors and the second optical sensors is measured, so that the user wearing status can be determined more accurately, to improve accuracy of detecting physiological data, for example, a heart rate, a blood pressure, and electrocardio.

In an optional embodiment, before the second optical transmitter transmits the laser light, the method further includes: A first optical transmitter transmits infrared light; the first optical sensors receive the infrared light; the wearing status of the wearable device is determined based on the infrared light signal received by the first optical sensors; when the wearing status of the wearable device is worn, the second optical transmitter transmits the laser light; the first optical sensors and the second optical sensors detect the laser light that is reflected; and the wearing status of the wearable device is determined based on the laser signals detected by the first optical sensors and the second optical sensors. In this case, based on the IR reflection feature, whether a user has worn the wearable device is first detected, and then the VCSEL is used to detect tightness of wearing after the wearable device is worn. The VCSEL reflection feature detection is enabled mainly in the loosely-worn scenario, and in this way, power consumption of the system is not considerably increased.

In an optional embodiment, the wearable device includes a capacitive sensor, and the capacitive sensor is configured to detect contact capacitance; and before the second optical transmitter transmits the laser light, the method further includes: The wearing status of the wearable device is determined based on the contact capacitance detected by the capacitive sensor; when the wearing status of the wearable device is worn, the second optical transmitter transmits the laser light; the first optical sensors and the second optical sensors detect the laser light that is reflected; and the wearing status of the wearable device is determined based on the laser signals detected by the first optical sensors and the second optical sensors. In this case, by using the capacitive sensor, whether the user has worn the wearable device is first detected, and then the VCSEL is used to detect tightness of wearing after the wearable device is worn. The VCSEL reflection feature detection is enabled mainly in the loosely-worn scenario, and in this way, power consumption of the system is not considerably increased.

In an optional embodiment, that the wearing status of the wearable device is determined based on the laser signals detected by the first optical sensors and the second optical sensors specifically includes: When a quantity of first optical sensors that have received the laser light is 0, and a quantity of second optical sensors that have received the laser light is greater than or equal to 1, it is determined that the wearing status of the wearable device is comfortably-worn; or when a quantity of first optical sensors that have received the laser light is greater than or equal to 1, and a quantity of second optical sensors that have received the laser light is greater than or equal to 1, it is determined that the wearing status of the wearable device is loosely-worn.

In an optional embodiment, that the wearing status of the wearable device is determined based on the laser signals detected by the first optical sensors and the second optical sensors specifically includes:

When a quantity of first optical sensors that have received the laser light is 0, and a quantity of second optical sensors that have received the laser light is greater than or equal to 2, it is determined that the wearing status of the wearable device is comfortably-worn; or when a quantity of first optical sensors that have received the laser light is greater than or equal to 1, and a quantity of second optical sensors that have received the laser light is greater than or equal to 1, it is determined that the wearing status of the wearable device is loosely-worn.

In an optional embodiment, that the wearing status of the wearable device is determined based on the laser signals detected by the first optical sensors and the second optical sensors specifically includes: The wearing status of the wearable device is determined based on a quantity of first optical sensors that detect the laser light and a quantity of second optical sensors that detect the laser light; and when the wearing status of the wearable device is not loosely-worn, the wearing status of the wearable device is further determined based on the infrared light signal received by the first optical sensors, the contact capacitance detected by the capacitive sensor, the quantity of first optical sensors that detect the laser light, and the quantity of second optical sensors that detect the laser light. The status is determined comprehensively based on detection results of the contact capacitance, the IR reflection feature, and the VCSEL reflection feature, so that accuracy of wearing status detection can be further improved.

In an optional embodiment, when the wearing status of the wearable device is worn, the method further includes: The first optical transmitter transmits at least one color of light; the first optical sensors receive the at least one color of light; and the wearing status of the wearable device is determined based on a signal of the at least one color of light received by the first optical sensors. By further using living body detection, accuracy of determining a wearing status can be further improved.

In an optional embodiment, the method further includes: When the wearing status of the wearable device is comfortably-worn, the wearing status is displayed.

In an optional embodiment, the method further includes: When the wearing status of the wearable device is loosely-worn, first prompt information is displayed, where the first prompt information is used to prompt that the user is wearing the device too loosely currently.

A third aspect provides a computer-readable storage medium. The computer-readable storage medium stores a computer program, and when the computer program is executed by a processor, the method according to the second aspect is implemented.

A fourth aspect provides a computer program product that includes instructions, and when the instructions in the computer program product are run on a computer, the computer is enabled to perform the method according to the second aspect.

DESCRIPTION OF EMBODIMENTS

Figure 1:
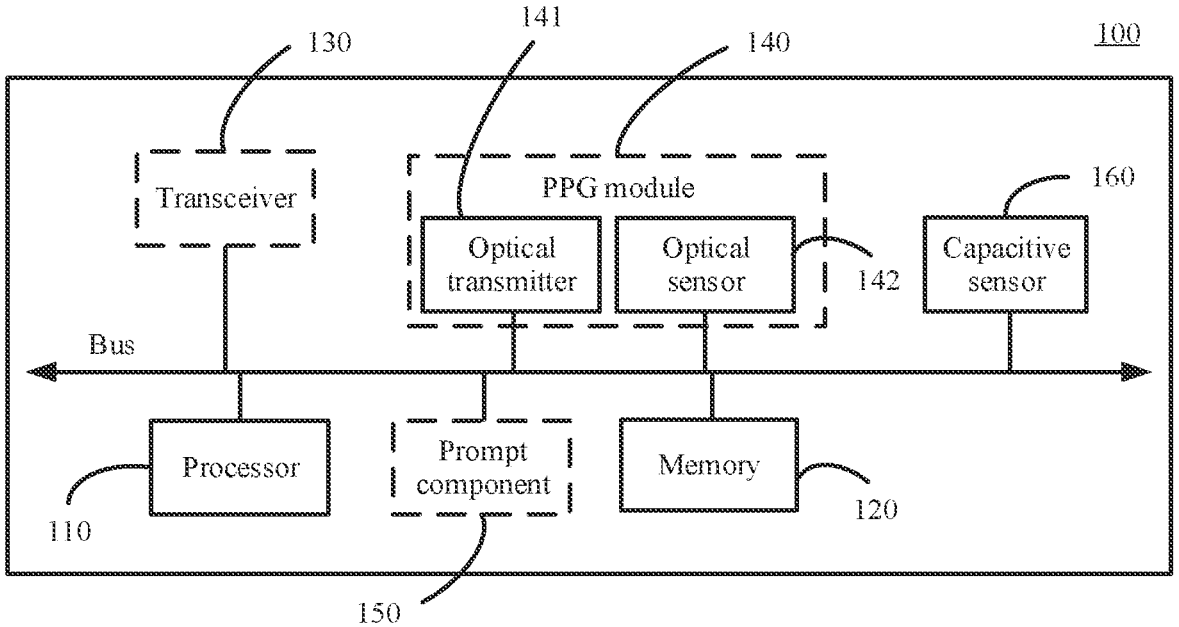
FIG. 1 is a schematic diagram of a structure of a wearable device according to an embodiment of this application.

Embodiments of this application are described below with reference to the accompanying drawings in embodiments of this application. Clearly, the described embodiments are merely some of rather than all embodiments of this application.

The terms "first", "second", and the like used below are merely for ease of description, and shall not be understood as an indication or implication of relative importance or an implicit indication of a quantity of indicated technical features. Therefore, a feature limited by "first", "second", and the like may explicitly indicate or implicitly include one or more such features. In the descriptions of this application, unless otherwise stated, "a plurality of" means two or more than two.

In addition, in embodiments of this application, "up", "down", "left", and "right" are not limited to definitions relative to directions in which components are schematically placed in the accompanying drawings. It should be understood that these directional terms may be relative concepts used for relative description and clarification, and may change correspondingly based on a change of a direction in which a component in the accompanying drawings is placed.

In this application, unless otherwise clearly specified and limited, the term "connection" should be understood in a broad sense. For example, a "connection" may be a fixed connection, a detachable connection, or integration, may be a direct connection, or may be an indirect connection through an intermediate medium. In addition, the term "electrical connection" may be a direct electrical connection, or may be an indirect electrical connection through an intermediate medium.

As functions of wearable devices are diversified and improved, a wearable device has increasingly become an essential electronic device for human. Generally, working modes of a wearable device are different when the wearable device is in a worn state and in a non-worn state. For example, when the wearable device is in the worn state, all functions of the device may be supported, while when the wearable device is in the non-worn state, some non-essential applications may be disabled to reduce power consumption of the wearable device and prolong a standby time of the device. In this case, it is particularly important to identify whether the wearable device is in the worn state or in the non-worn state.

At present, a wearing detection method that is used is usually to detect, based on an IR light source and a PD module that are used for heart rate measurement, whether the wearable device is blocked by an object. The light source and the PD module used for heart rate measurement are also referred to as a photoplethysmography (Photoplethysmography. PPG) module (referred to as a PPG module below). A measurement principle of this method is to utilize a reflection feature of light. When a front is blocked, there is a high light reflectivity. Specifically, the IR light source transmits infrared light. The PD receives the reflected light that is reflected by skin. Then, a processor of the wearable device performs processing and calculation to obtain wearing detection information. If it is detected that there is a blocking object, it is considered that the wearable device is currently in the worn state. However, in the foregoing method, the identification that the wearable device is blocked by an object is not completely equivalent to the fact that the wearable device is in the worn state. For example, when a user places the wearable device on another object and is not wearing the wearable device, the IR light source and PD module identifies that the wearable device is blocked by an object, and as a result, a status is falsely determined. Consequently, an error occurs for a working mode that the wearable device enters or an application that is enabled/disabled based on the worn state. In other words, in the wearing detection method, human skin and a surface of another material cannot be differentiated effectively, leading to false determining about wearing.

To resolve the problem of falsely determining a wearing status, on the basis of the foregoing optical reflection solution, a capacitive sensor is used in combination to detect whether the wearable device is worn on a human body, to effectively improve accuracy of wearing detection. Different substances have different dielectric constants, and a dielectric constant is one of the key factors that determine a capacitance value of a parallel-plate capacitor. Therefore, a capacitance value acquired by the capacitive sensor can be used to effectively distinguish most textures with a dielectric constant that is different from that of a human body. However, a difference between dielectric constants of a metal and a human body are rather little. As a result, there is still false wearing detection with metals.

Moreover, the optical reflection solution has a high requirement on a wearing posture with the wearable device. Even if a user has normally worn the wearable device, if the wearable device is worn loosely, an optical path is easily interfered by external ambient light or the like in this loosely-worn scenario, and false determining is still caused.

In view of the problems, an embodiment of this application provides a wearable device supporting wearing detection. A vertical-cavity surface-emitting laser (Vertical-Cavity Surface-Emitting Laser, VCSEL) and corresponding optical sensors are further used. The corresponding optical sensors are configured to detect laser light transmitted by the VCSEL, and whether a user has worn the wearable device is determined based on a quantity and locations of optical sensors that detect the laser light. In some embodiments of this application, whether the user has worn the wearable device can be correctly determined only using the VCSEL and the optical sensors around the VCSEL. As power consumption of the VCSEL is high, in some other embodiments, based on the VCSEL and the optical sensors around the VCSEL, a capacitive sensor or an existing PPG module may be further used in combination. On a basis that the capacitive sensor or the existing PPG module preliminarily determines that the user has worn the wearable device, the VCSEL is enabled to further determine whether the user is wearing the wearable device comfortably or loosely. The optical transmitter, VCSEL, (referred to as a second optical transmitter below) and the optical sensors (referred to as second optical sensors below) are disposed right in the middle of the PPG module, and original optical sensors (referred to as first optical sensors below) of the PPG module are disposed around a light source (referred to as a first optical transmitter below). With normal comfortable wearing, because the VCSEL has features such as perfect light beam quality and a small field of view, after a light beam transmitted by the VCSEL is reflected by skin, all light rays are reflected back to the second optical sensors around the VCSEL to generate a current, while no light ray is reflected to the first optical sensors around the PPG module to generate a light current. However, in a scenario in which the user is wearing the wearable device loosely, because naturally there is a specific included angle between the PPG module and an arm, after the light transmitted by the VCSEL is reflected by skin, a light ray not only falls on the second optical sensors around the VCSEL, but also falls on the first optical sensors of the PPG module. The generated light current in the first optical sensors of the PPG module is measured, so that it can be determined that a wearing posture of the user is incorrect, and the user is prompted for normal wearing, to improve wearing experience, and improve accuracy of detecting a heart rate, a blood pressure, electrocardio, and the like.

The wearable device provided in this application may be a smartwatch, a smart band, or the like, may be worn by a user on a wrist, and is configured to detect physiological data of the user, for example, electrocardio, a blood pressure, saturation of blood oxygen, and an electrocardiogram.

FIG. 1 is a schematic diagram of a structure of a wearable device according to an embodiment of this application. As shown in FIG. 1, the wearable device 100 includes a processor 110, a memory 120, a PPG module 140, and a capacitive sensor 160. The PPG module 140 includes an optical transmitter 141 and an optical sensor 142. The processor 110, the memory 120, the PPG module 140, and the capacitive sensor 160 may be connected through a bus. There may be one or more optical transmitters 141 and one or more optical sensors 142. The optical transmitter 141 is configured to transmit at least one color of light or laser light. At least one optical transmitter 141 is a VCSEL, and is configured to transmit laser light, while a remaining optical transmitter 141 transmits one or more colors of light, for example, red light, green light, or infrared light. The optical sensor 142 is configured to detect the at least one color of light or laser light. The optical sensor 142 is coupled to the processor 110, to transmit the detected light to the processor 110. For example, the optical sensor 142 is connected to the processor 110 through the bus. The capacitive sensor 160 is configured to: detect a capacitance value, and determine, based on the capacitance value, whether the wearable device is worn on a skin surface of a human body. The capacitive sensor 160 is coupled to the processor 110, to transmit the detected capacitance value to the processor 110. For example, the capacitive sensor 160 is connected to the processor 110 through the bus. The memory 120 is configured to store a program and data. The processor 110 is configured to: execute the program stored in the memory 120, read the data stored in the memory 120, and determine a wearing status of the wearable device based on one or more of the laser light or the infrared light detected by the optical sensor 142, the capacitance value detected by the capacitive sensor 160, and the like. Further, the processor 110 may detect a heart rate, a blood pressure, saturation of blood oxygen, and an electrocardiogram with reference to the wearing status of the wearable device.

In an optional embodiment, the wearable device 100 may further include a transceiver 130. The transceiver is configured to communicate with another electronic device. The another electronic device includes a mobile phone or a tablet. For example, the wearable device 100 may transmit a determined wearing state to the another electronic device by using the transceiver 130.

In another optional embodiment, the wearable device 100 may further include a prompt component 150. The prompt component 150 is connected to the processor 110, and is configured to generate prompt information based on an indication of the processor. The prompt information is used to prompt the wearing status of the wearable device. For example, the prompt component 150 may be a display, and the prompt information may indicate the wearing status of the wearable device with an image and text to a user. For another example, the prompt component 150 may alternatively be a loudspeaker, and the prompt information may indicate the wearing status of the wearable device with audio to a user. For another example, the prompt component 150 may be a buzzer, and the prompt information may indicate the wearing status of the wearable device with vibration to a user. For another example, the prompt component 150 is configured to prompt a user when the wearing status of the wearable device 100 is loosely-worn.

Figure 2:
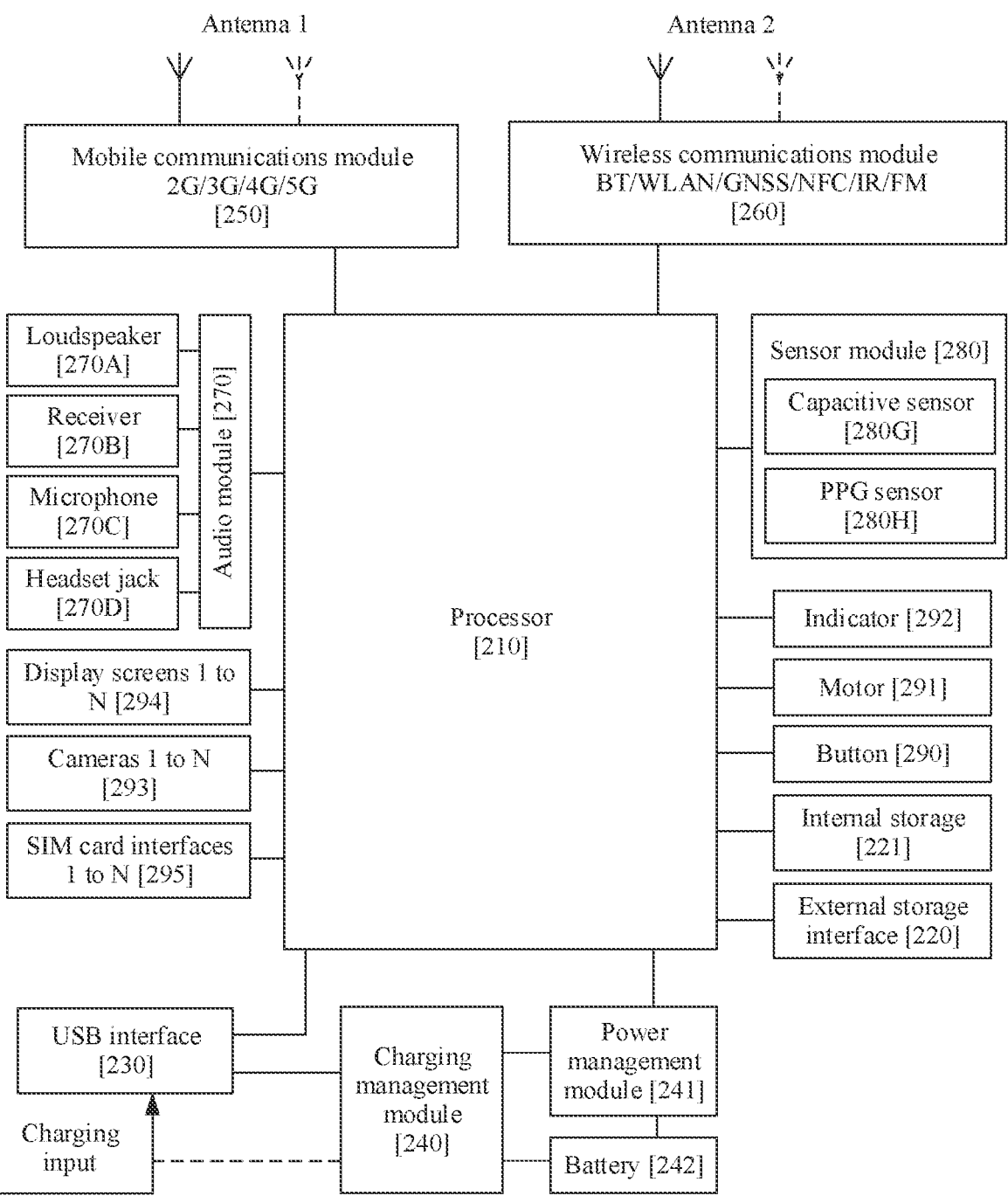
FIG. 2 is a schematic diagram of a structure of a wristband according to an embodiment of this application.

This application is further described below by using a wristband 200 as an example of the wearable device 100. FIG. 2 is a schematic diagram of a structure of a wristband according to an embodiment of this application.

The wristband 200 may include a processor 210, an external storage interface 220, an internal storage 221, a universal serial bus (universal serial bus, USB) interface 230, a charging management module 240, a power management module 241, a battery 242, an antenna 1, an antenna 2, a mobile communications module 250, a wireless communications module 260, an audio module 270, a loudspeaker 270A, a receiver 270B, a microphone 270C, a headset jack 270D, a sensor module 280, a button 290, a motor 291, an indicator 292, a camera 293, a display screen 294, a subscriber identity module (subscriber identity module, SIM) card interface 295, and the like. The sensor module 280 may include a capacitive sensor 280G, a PPG sensor 280H, and the like.

It can be understood that the structure shown in this embodiment of this application does not constitute a specific limitation on the wristband 200. In some other embodiments of this application, the wristband 200 may include more or fewer components than those shown in the figure, combine some components, split some components, or have different component arrangements. The components shown in the figure may be implemented by hardware, software, or a combination of software and hardware.

The processor 210 may include one or more processing units. For example, the processor 210 may include an application processor (application processor, AP), a modem processor, a graphics processing unit (graphics processing unit, GPU), an image signal processor (image signal processor, ISP), a controller, a video codec, a digital signal processor (digital signal processor, DSP), a baseband processor, and/or a neural-network processing unit (neural-network processing unit, NPU). Different processing units may be independent components, or may be integrated into one or more processors. The controller may generate an operation control signal based on an instruction operation code and a time sequence signal, to complete control of instruction reading and instruction execution.

A memory may be further disposed in the processor 210, and is configured to store an instruction and data. In some embodiments, the memory in the processor 210 is a cache memory. The memory may store an instruction or data that has just been used or is cyclically used by the processor 210. If the processor 210 needs to use the instruction or the data again, the processor may directly invoke the instruction or the data from the memory. This avoids repeated access, reduces a time for waiting of the processor 110, and improves system efficiency.

The USB interface 230 is an interface that conforms to a USB standard specification, and may be specifically a mini USB interface, a micro USB interface, a USB Type-C interface, or the like. The USB interface 230 may be used to connect to a charger for charging the wristband 200, may be used to transmit data between the wristband 200 and a peripheral device, or may be used to connect to a headset for playing audio through the headset. The interface may be further used to connect to another electronic device, for example, an AR device.

The charging management module 240 is configured to receive a charging input from a charger. The charger may be a wireless charger or a wired charger. In some embodiments of wired charging, the charging management module 240 may receive a charging input from a wired charger through the USB interface 230. In some embodiments of wireless charging, the charging management module 240 may receive a wireless charging input through a wireless charging coil of the wristband 200. The charging management module 240 supplies power to the electronic device by using the power management module 241 while charging the battery 242.

The power management module 241 is configured to connect to the battery 242, the charging management module 240, and the processor 210. The power management module 241 receives an input from the battery 242 and/or the charging management module 240, and supplies power to the processor 210, the internal storage 221, the display screen 294, the camera 293, the wireless communications module 260, and the like. The power management module 241 may be further configured to monitor parameters such as a battery capacity, a battery cycle count, and a battery state of health (electric leakage and impedance). In some other embodiments, the power management module 241 may alternatively be disposed in the processor 210. In some other embodiments, the power management module 241 and the charging management module 240 may be alternatively disposed in a same component.

A wireless communications function of the wristband 200 may be implemented by using the antenna 1, the antenna 2, the mobile communications module 250, the wireless communications module 260, the modem processor, the baseband processor, and the like.

The antenna 1 and the antenna 2 are configured to transmit and receive an electromagnetic wave signal. Each antenna in the electronic device 100 may be configured to cover one or more communications frequency bands. Different antennas may be further reused, to improve antenna utilization. For example, the antenna 1 may be reused as a diversity antenna in a wireless local area network. In some other embodiments, the antenna may be used in combination with a tuning switch.

The mobile communications module 250 may provide a wireless communications solution including 2G/3G/4G/5G that is applied to the wristband 200. The mobile communications module 250 may include at least one filter, a switch, a power amplifier, a low noise amplifier (low noise amplifier, LNA), and the like. The mobile communications module 250 may receive an electromagnetic wave through the antenna 1, perform processing, for example, filtering or amplification on the received electromagnetic wave, and transmit the electromagnetic wave to the modem processor for demodulation. The mobile communications module 250 may further amplify a signal modulated by the modem processor, and convert the signal into an electromagnetic wave for radiation through the antenna 1. In some embodiments, at least a part of functional modules of the mobile communications module 250 may be disposed in the processor 210. In some embodiments, at least a part of functional modules of the mobile communications module 250 and at least a part of modules of the processor 210 may be disposed in a same component.

The wireless communications module 260 may provide a wireless communications solution that is applied to the wristband 200 and that includes a wireless local area network (wireless local area network, WLAN) (for example, a wireless fidelity (wireless fidelity, Wi-Fi) network), Bluetooth (Bluetooth, BT), a global navigation satellite system (global navigation satellite system, GNSS), frequency modulation (frequency modulation, FM), a near field communication (near field communication, NFC) technology, an infrared (infrared, IR) technology, and the like. The wireless communications module 260 may be one or more components integrating at least one communications processor module. The wireless communications module 260 receives an electromagnetic wave through the antenna 2, performs frequency modulation and filtering on an electromagnetic wave signal, and transmits a processed signal to the processor 210. The wireless communications module 260 may further receive a to-be-transmitted signal from the processor 210, perform frequency modulation and amplification on the signal, and convert the signal into an electromagnetic wave for radiation through the antenna 2.

In some embodiments, in the wristband 200, the antenna 1 and the mobile communications module 250 are coupled, and the antenna 2 and the wireless communications module 260 are coupled, so that the wristband 200 can communicate with a network and another device by using a wireless communications technology. The wireless communications technology may include a global system for mobile communications (global system for mobile communications, GSM), a general packet radio service (general packet radio service, GPRS), code division multiple access (code division multiple access, CDMA), wideband code division multiple access (wideband code division multiple access, WCDMA), time division-synchronous code division multiple access (time division-synchronous code division multiple access, TD-SCDMA), long term evolution (long term evolution, LTE), BT, a GNSS, a WLAN, NFC, FM, IR, and/or the like. The GNSS may include a global positioning system (global positioning system, GPS), a global navigation satellite system (global navigation satellite system, GLONASS), a BeiDou navigation satellite system (BeiDou navigation satellite system, BDS), a quasi-zenith satellite system (quasi-zenith satellite system, QZSS), and/or a satellite based augmentation system (satellite based augmentation system, SBAS).

The wristband 200 may implement a display function by using the GPU, the display screen 194, the application processor, and the like. The GPU is a microprocessor for image processing, and is connected to the display screen 294 and the application processor. The GPU is configured to: perform mathematical and geometric computation, and render an image. The processor 210 may include one or more GPUs that execute a program instruction to generate or change display information.

The display screen 294 is configured to display an image, a video, or the like. The display screen 294 includes a display panel. The display panel may use a liquid crystal display (liquid crystal display, LCD), an organic light-emitting diode (organic light-emitting diode, OLED), an active-matrix organic light-emitting diode (active-matrix organic light-emitting diode, AMOLED), a flexible light-emitting diode (flex light-emitting diode, FLED), a mini-LED, a micro-LED, a micro-OLED, a quantum dot light-emitting diode (quantum dot light-emitting diode, QLED), and the like. In some embodiments, the wristband 200 may include one or N display screens 294, where N is a positive integer greater than 1.

On the display screen 294, with program control of the processor 210, prompt information, for example, a wearing manner and a wearing status, and historical information about detected physiological data, for example, a heart rate, that is in a visual (numeric, tabular, or graphical) or audible (synthetic speech or tone) form may be provided. As a non-limiting example, a visual curve diagram may be displayed. The visual curve diagram shows a heart rate calculated every 5 minutes during a previous fixed time interval (for example, 1 hour) or after an exercise time period has ended (as determined by an indication from a user). On the display screen 294, with control of the processor 210, information about an average heart rate or statistical information about a heart rate during one or more previous time periods may be further provided. In another example, a current heart rate value may be provided on the display screen 294 as a "real-time" heart rate value that is displayed to a user periodically (for example, every second) during an ongoing process for an exercise plan.

The wristband 200 may implement a photographing function by using the ISP, the camera 293, the video codec, the GPU, the display screen 294, the application processor, and the like.

The ISP is configured to process data fed back by the camera 293. For example, during photographing, a shutter is pressed, and a light ray is transmitted to a photosensitive element of the camera through a lens. An optical signal is converted into an electrical signal, and the photosensitive element of the camera transmits the electrical signal to the ISP for processing, to convert the electrical signal into a visible image. The ISP may further perform algorithm optimization on noise, brightness, and complexion of the image. The ISP may further optimize parameters such as exposure and a color temperature in a photographing scenario. In some embodiments, the ISP may be disposed in the camera 293.

The camera 293 is configured to capture a static image or a video. An optical image of an object is generated through the lens, and is projected onto the photosensitive element. The photosensitive element may be a charge coupled device (charge coupled device, CCD) or a complementary metal-oxide-semiconductor (complementary metal-oxide-semiconductor, CMOS) photoelectric transistor. The photosensitive element converts an optical signal into an electrical signal, and then transmits the electrical signal to the ISP for converting the electrical signal into a digital image signal. The ISP outputs the digital image signal to the DSP for processing. The DSP converts the digital image signal into an image signal in a standard format, for example, RGB or YUV. In some embodiments, the wristband 200 may include one or N cameras 293, where N is a positive integer greater than 1.

The digital signal processor is configured to process a digital signal, and may process another digital signal in addition to the digital image signal. For example, when the wristband 200 selects a frequency, the digital signal processor is configured to perform Fourier transform on frequency point energy.

The video codec is configured to compress or decompress a digital video. The wristband 200 may support one or more types of video codecs. Therefore, the wristband 200 may play or record videos in a plurality of encoding formats, for example, moving picture experts group (moving picture experts group, MPEG)-1, MPEG-2, MPEG-3, and MPEG4.

The NPU is a neural-network (neural-network, NN) computing processor that quickly processes input information by referring to a structure of a biological neural network, for example, by referring to a mode of transmission between human brain neurons, and may further continuously perform self-learning. Applications such as intelligent cognition of the wristband 200, for example, image recognition, facial recognition, speech recognition, and text understanding, may be implemented by using the NPU.

The external storage interface 220 may be used to connect to an external storage card, for example, a micro SD card, to extend a storage capability of the wristband 200. The external storage card communicates with the processor 210 through the external storage interface 220, to implement a data storage function. For example, files such as music and a video are stored in the external storage card.

The internal storage 221 may be configured to store computer-executable program code. The executable program code includes an instruction. The internal storage 221 may include a program storage area and a data storage area. The program storage area may store an operating system, an application required for at least one function (for example, a sound playback function or an image play function), and the like. The data storage area may store data (for example, audio data and an address book) and the like that are created during use of the wristband 200. In addition, the internal storage 221 may include a high-speed random access memory, and may further include a non-volatile memory, for example, at least one magnetic disk storage device, a flash storage device, or a universal flash storage (universal flash storage, UFS). The processor 210 runs the instruction stored in the internal storage 221 and/or an instruction stored in the memory disposed in the processor, to implement various function applications and data processing of the wristband 200.

The wristband 200 may implement an audio function, for example, music play or recording, by using the audio module 270, the loudspeaker 270A, the receiver 270B, the microphone 270C, the headset jack 270D, the application processor, and the like.

The audio module 270 is configured to convert digital audio information into an analog audio signal for output, and is further configured to convert an analog audio input into a digital audio signal. The audio module 270 may be further configured to encode and decode an audio signal. In some embodiments, the audio module 270 may be disposed in the processor 210, or a part of functional modules of the audio module 270 are disposed in the processor 210.

The loudspeaker 270A, also referred to as a "speaker", is configured to convert an electrical audio signal into a sound signal. The wristband 200 may play music or implement a hands-free call by using the loudspeaker 270A.

The receiver 270B, also referred to as an "earpiece", is configured to convert an electrical audio signal into a sound signal. When a call or audio information is received by the wristband 200, the receiver 270B may be put close to a human ear to listen to a voice.

The microphone 270C, also referred to as a "mike" or "mic", is configured to convert a sound signal into an electrical signal. When making a call or sending a voice message, a user may move the mouth close to the microphone 270C and make a sound, to input a sound signal to the microphone 270C. At least one microphone 270C may be disposed in the wristband 200. In some other embodiments, two microphones 270C may be disposed in the wristband

200, to acquire a sound signal and further reduce noises. In some other embodiments, three, four, or more microphones 270C may alternatively be disposed in the wristband 200, to acquire a sound signal, reduce noises, and identify a sound source, to implement a directional sound recording function and the like.

The headset jack 270D is configured to connect to a wired headset. The headset jack 270D may be the USB interface 230, or may be a 3.5 mm open mobile terminal platform (open mobile terminal platform, OMTP) standard interface or a cellular telecommunications industry association of the USA (cellular telecommunications industry association. CTIA of the USA) standard interface.

The capacitive sensor 280G includes a parallel-plate capacitor having two plates. One of the plates is disposed on a surface of the wristband 200, and the other plate may be disposed on a flexible printed circuit (Flexible Printed Circuit, FPC). After the plate disposed on the surface of the wristband 200 contacts skin of a user or an object with another texture, the capacitive sensor 280G can detect a change of a capacitance value, and whether the wristband 200 has been worn is determined based on the capacitance value. For example, it is detected whether the capacitance value detected by the capacitive sensor 280G is within a preset capacitance value range. When the preset capacitance value is within the preset capacitance value range, it is determined that the wristband 200 has been worn. As a capacitance value of a parallel-plate capacitor mainly depends on an area of plates and a distance between the plates, and a distance between the foregoing two plates is short, to obtain a larger capacitance input signal, it is generally considered that an area of the plate disposed on the surface of the wristband 200 needs to be designed as large as possible.

The PPG sensor 280H includes an optical transmitter and an optical sensor. Heart rate measurement by using the PPG sensor 280H is performed based on a principle of light absorption of substances. The optical transmitter of the PPG sensor 280H projects light upon blood vessels under skin, and the optical sensor receives a light ray transmitted from the skin. Because blood of different volumes in the blood vessels absorbs light differently, when the heart beats, blood flow increases, and light absorption increases accordingly, while between each heartbeat, the blood flow decreases, and the light absorption decreases accordingly. Therefore, a heart rate can be measured based on absorbency of blood. In an operation, the optical transmitter may transmit a light beam to skin of a user, and the light beam may be reflected by the skin of the user and received by the optical sensor. The optical sensor may convert the light into an electrical signal indicating intensity of the light. The electrical signal may be in an analog form, and may be converted into a digital form by an analog-to-digital converter. A digital signal from the analog-to-digital converter may be a time-domain PPG signal that is fed into the processor 210. The processor 210 may receive the digital signal from the optical sensor, and may process the signal to provide a heart rate or wearing status output signal for a memory, a visual display, an audible annunciator, a touchscreen, or another output indicator. In some embodiments, the PPG sensor 280H is used to form the foregoing PPG module for measuring physiological data, for example, a heart rate. The optical transmitter that transmits laser light may be disposed at a central position of the PPG sensor 280H. The optical sensor that detects the reflected laser light may be disposed around the optical transmitter that transmits the laser light. The optical transmitter that measures physiological data, for example, a heart rate, and the optical sensor are disposed around an optical sensor that detects the laser light.

A pressure sensor, a gyroscope, an acceleration sensor, an ambient optical sensor, a barometer, a hygrometer, a thermometer, an infrared sensor, or another sensor may be further configured on the wristband 200. Details are not described herein.

The button 290 includes a power button, a volume button, and the like. The button 290 may be a mechanical button, or may be a touch button. The wristband 200 may receive a button input, and generate a keying signal input related to user settings and function control on the wristband 200.

The motor 291 may generate a vibration prompt. The motor 291 may be configured to produce an incoming call vibration prompt, and may be configured to provide touch vibration feedback. For example, touch operations performed for different applications (for example, taking a picture and playing audio) may correspond to different vibration feedback effects. For touch operations performed on different areas of the display screen 294, the motor 291 may also correspond to different vibration feedback effects. Different application scenarios (for example, time reminding, information receiving, an alarm clock, and a game) may also correspond to different vibration feedback effects. A touch vibration feedback effect may be further customized.

The indicator 292 may be an indicator light, may be configured to indicate a charging status and a power change, and may be configured to indicate a message, a missed call, a notification, and the like.

The SIM card interface 295 is used to connect a SIM card. The SIM card may be inserted into the SIM card interface 295 or removed from the SIM card interface 295, to implement contact with or separation from the wristband 200. The wristband 200 may support one or N SIM card interfaces, where N is a positive integer greater than 1. The SIM card interface 295 may support a nano-SIM card, a micro-SIM card, a SIM card, and the like. A plurality of cards may be inserted into a same SIM card interface 295 at the same time. The plurality of cards may be of a same type or of different types. The SIM card interface 295 is compatible with different types of SIM cards. The SIM card interface 295 is also compatible with an external storage card. The wristband 200 interacts with a network by using the SIM card, to implement functions such as calling and data communication. In some embodiments, the wristband 200 uses an eSIM, that is, an embedded SIM card. The eSIM card may be embedded into the wristband 200, and cannot be separated from the wristband 200.

Figures 3, 4:
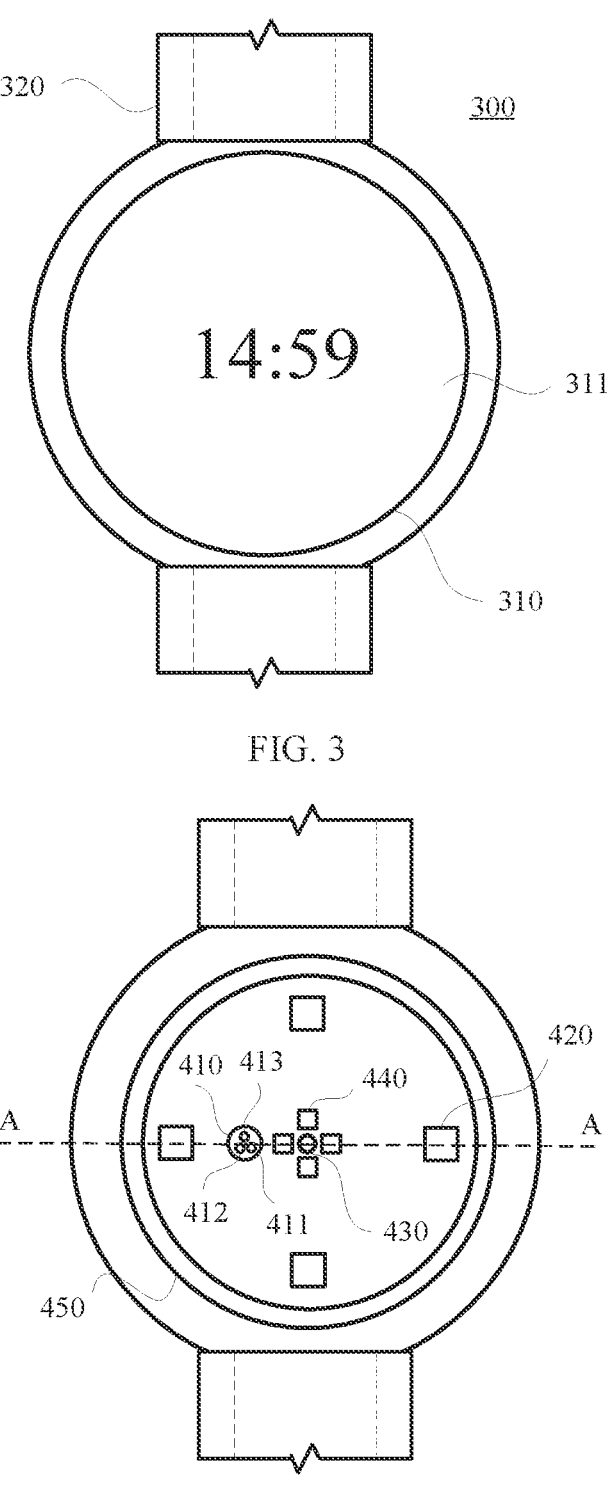
FIG. 3 is a top view of an implementation of a smartwatch according to an embodiment of this application.
FIG. 4 is a bottom view of an implementation of the smartwatch shown in FIG. 3.
Figures 6, 7:
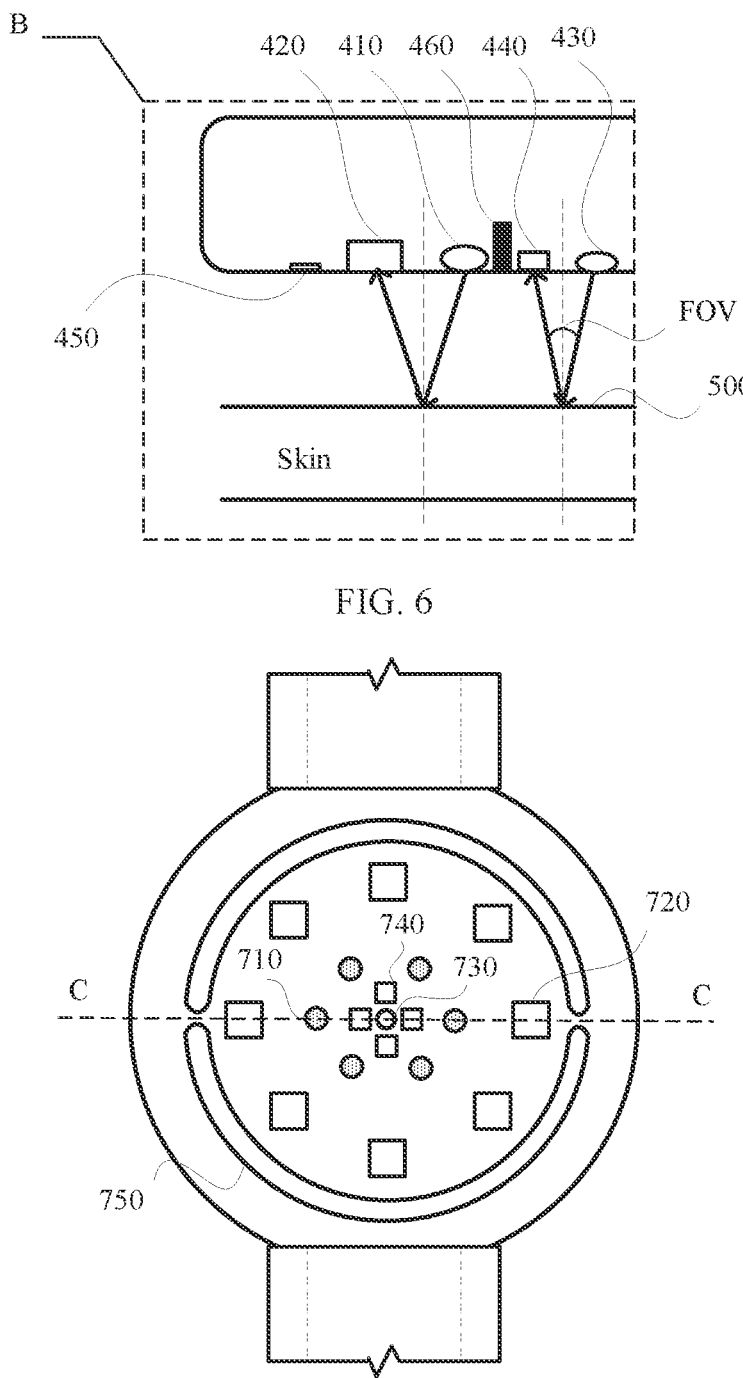
FIG. 6 is an enlarged schematic diagram of a structure at B in FIG. 5.
FIG. 7 is a bottom view of another implementation of the smartwatch shown in FIG. 3.

This application is further described below by using a smartwatch as an example of the wristband 200. FIG. 3 is a schematic diagram of a structure of a smartwatch according to an embodiment of this application. As shown in FIG. 3, the smartwatch 300 includes a watch face 310 and a watch strap 320. A front side of the watch face 310 includes a display screen 311. The display screen 311 is configured to display information, for example, time, a motion status, a physical index of a wearer, or a wearing status. As shown in FIG. 4 and FIG. 7, optical transmitters and optical sensors are disposed on a back side of the watch face 310. The smartwatch may be worn on a wrist by using the watch strap 320. In this case, the back side of the watch face 310 is attached to skin.

As shown in FIG. 4, the smartwatch includes one first optical transmitter 410 and four first optical sensors 420. A light-emitting element of the first optical transmitter 410 includes a green LED 411, a red LED 412, and an infrared LED 413. The optical transmitter 410 may transmit green light, red light, and infrared light by using the green LED 411, the red LED 412, and the infrared LED 413 respectively. The LED is merely an example of the light-emitting element, and the LED may alternatively be another light-emitting component, for example, a VCSEL. One or more of green light, red light, and infrared light may be transmitted toward a direction of a wrist by using the first optical transmitter 410. Reflected light that is obtained after the light transmitted by the optical transmitter 410 is reflected by the wrist is received by the first optical sensors 420. For example, the first optical transmitter 410 and the first optical sensors 420 form a PPG module of the smartwatch for detecting physiological data of a user wearing the smartwatch, for example, a heart rate and saturation of blood oxygen.

Figure 5A:
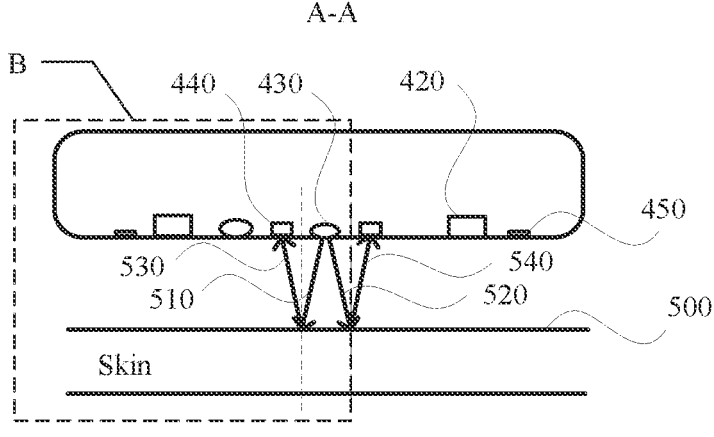
FIG. 5A is a sectional view, cut along A-A, of the smartwatch shown in FIG. 4 that is comfortably worn on a wrist of a user.
Figure 5B:
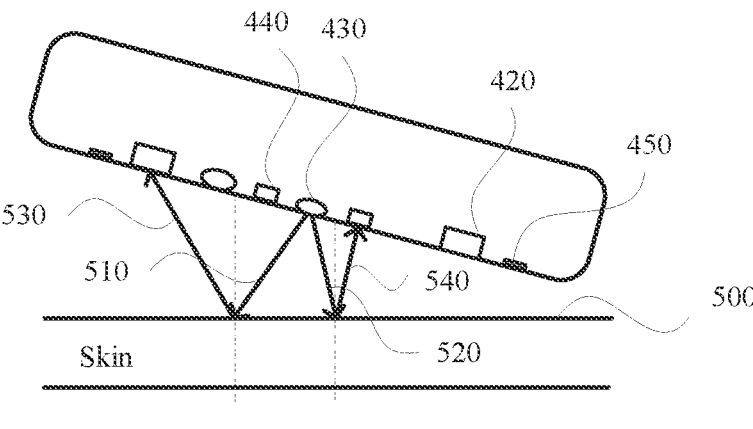
FIG. 5B is a sectional view, cut along A-A, of the smartwatch shown in FIG. 4 that is loosely worn on a wrist of a user.

Further refer to FIG. 4. The smartwatch further includes one second optical transmitter 430 and four second optical sensors 440. The second optical transmitter 430 is a light-emitting component VCSEL, and is disposed at a central position on the back side of the watch face. The four second optical sensors 440 are evenly disposed around the second optical transmitter 430, and each of the second optical sensors 440 is disposed between the second optical transmitter 430 and a corresponding first optical sensor 420. In this example, the four first optical sensors 420 are disposed in a one-to-one correspondence with the four second optical sensors 440 in the four directions of up, down, left, and right respectively. As shown in FIG. 5A, in a comfortably-worn scenario, a plane on which the back side of the watch face is located is parallel to a surface 500 that is in contact with a human body. Because the light-emitting component VCSEL has features such as perfect light beam quality and a small field of view, after light beams 510 and 520 transmitted by the VCSEL are reflected by skin, all light rays are reflected back to the second optical sensors 440 around the VCSEL (see light beams 530 and 540 shown in FIG. 5A), and a light current is generated in the second optical sensors 440, while no light ray is reflected to the first optical sensors 420 to generate a light current. As shown in FIG. 5B, in a scenario in which a user is wearing the smartwatch 300 loosely, because there is a specific included angle between the back side of the watch face and an arm, after the light beams 510 and 520 transmitted by the VCSEL are reflected by skin, a light ray is not only reflected to the second optical sensors 440 around the VCSEL (see a light beam 530 shown in FIG. 5B), but is also reflected to the first optical sensors 420 (see a light beam 540 shown in FIG. 5B). The generated light current in the first optical sensors 420 is measured, so that it can be determined that a wearing posture of the user is incorrect, and the user is prompted for normal wearing, to improve wearing experience, and improve accuracy of detecting a heart rate, a blood pressure, saturation of blood oxygen, having an electrocardiogram, and the like. Further, as the four first optical sensors that correspond to the four second optical sensors are disposed in the four directions of up, down, left, and right, by detecting a direction in which a light current of one of the first optical sensors has increased, a direction in which wearing is loose can be determined.

Still refer to FIG. 4. The smartwatch further includes a capacitive sensor 450. The capacitive sensor 450 may be designed into a single ring as shown in FIG. 4, may be designed into two symmetric rings, or may be designed into a rectangle or another shape. The capacitive sensor 450 is used as one of plates of a parallel-plate capacitor, and the other plate may be disposed on a flexible printed circuit (FPC). As a capacitance value of the capacitive sensor 450 mainly depends on an area of plates and a distance between the plates, it is generally considered that an area of the capacitive sensor 450 needs to be designed as large as possible. By further using the capacitive sensor, whether the user has worn the wearable device is first detected, and then the VCSEL is used to detect tightness of wearing after the wearable device is worn, to enable VCSEL reflection feature detection mainly in a loosely-worn scenario. In this way, power consumption of a system is not considerably increased.

FIG. 6 is a partially enlarged schematic diagram of a structure at B in FIG. 5A. A shading wall 460 is disposed between the second optical sensors 440 and the first optical transmitter 410, mainly to prevent light leakage. Optionally, a shading wall may be further disposed between the second optical transmitter 430 and the second optical sensors 440, and between the first optical transmitter 410 and the first optical sensors 420, to avoid that light from a light source goes directly into an optical sensor. It can be learned from FIG. 6 that a light beam transmitted by the second optical transmitter 430 (VCSEL) has a small field of view (Field of View, FOV) that is usually 15° to 20°. Therefore, the light beam transmitted by the second optical transmitter 430 (VCSEL) is well collimated. When the user is wearing the smartwatch comfortably, the light beam transmitted by the second optical transmitter 430 (VCSEL), after being reflected by skin of the user, basically enters the second optical sensors 440 disposed around the second optical transmitter 430, and does not enter the first optical sensors 420 that are farther away from the second optical transmitter 430.

In another example, the first optical transmitter includes six monochromatic optical transmitters, and there are eight first optical sensors that are evenly distributed on the back side of the watch face, to more accurately determine a wearing status of the smartwatch.

Figure 8A:
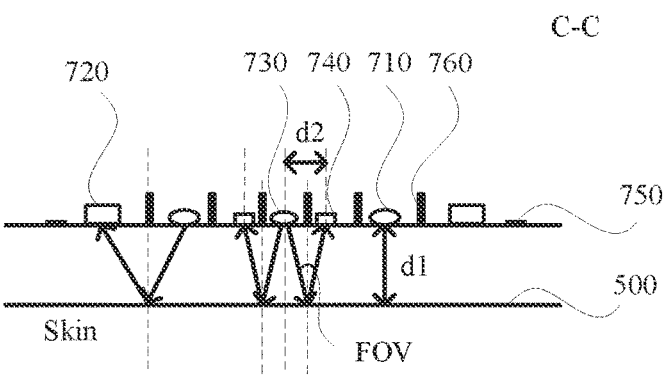
FIG. 8A is a sectional view, cut along C-C. of the smartwatch shown in FIG. 7 that is comfortably worn on a wrist of a user.

As shown in FIG. 7, the smartwatch includes six first optical transmitters 710 and eight first optical sensors 720. Each of the first optical transmitters 710 includes one light-emitting element, and the light-emitting element may be one of a green LED, a red LED, and an infrared LED. Optionally, the six optical transmitters 710 may include two green LEDs, two red LEDs, and two infrared LEDs that are arranged at intervals in order and that transmit green light, red light, and infrared light respectively. In some embodiments, a quantity of the first optical transmitters 710 is greater than or equal to 6. This is not limited in this embodiment of this application. One or more of green light, red light, and infrared light may be transmitted toward a direction of a wrist by using the first optical transmitters 710. As shown in FIG. 8A, reflected light that is obtained after the light transmitted by the first optical transmitters 710 is reflected by the wrist is received by the first optical sensors 720. For example, the first optical transmitters 710 and the first optical sensors 720 form a PPG module of the smartwatch for detecting physiological data of a user wearing the smartwatch, for example, a heart rate and saturation of blood oxygen.

Figure 8B:
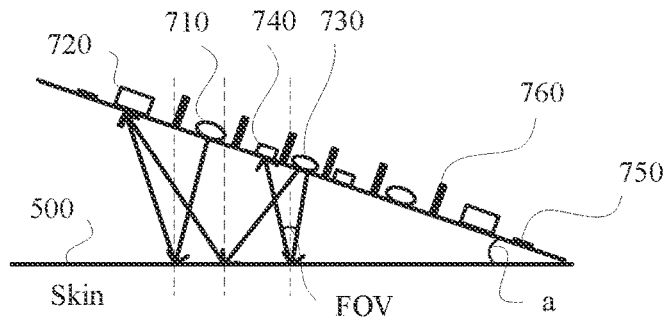
FIG. 8B is a sectional view, cut along C-C, of the smartwatch shown in FIG. 7 that is loosely worn on a wrist of a user.

Further refer to FIG. 7. The smartwatch further includes one second optical transmitter 730 and four second optical sensors 740. The second optical transmitter 730 is a light-emitting component VCSEL, and is disposed at a central position on the back side of the watch face. The four second optical sensors 740 are evenly distributed around the second optical transmitter 730, and are located between the second optical transmitter 730 and the first optical transmitters 710. In this example, the first optical sensors 720 are evenly disposed around the second optical transmitter 730, the second optical sensors 740, and the first optical transmitters 710. Four of the eight first optical sensors 720 are disposed in a one-to-one correspondence with the four second optical sensors 740 in the four directions of up, down, left, and right respectively. As shown in FIG. 8A, in a comfortably-worn scenario, a plane on which the back side of the watch face is located is parallel to a surface 500 that is in contact with a human body. Because the light-emitting component VCSEL has features such as perfect light beam quality and a small field of view, after a light beam transmitted by the VCSEL is reflected by skin, all light rays are reflected back to the second optical sensors 740 around the VCSEL, and a light current is generated, while no light ray is reflected to the first optical sensors 720 to generate a light current. As shown in FIG. 8B, in a scenario in which a user is wearing the smartwatch 300 loosely, because there is a specific included angle a between the back side of the watch face and an arm, after the light beam transmitted by the VCSEL is reflected by skin, a light ray is not only reflected to the second optical sensors 740 around the VCSEL, but is also reflected to the first optical sensors 720. The generated light current in the first optical sensors 720 is measured, so that it can be determined that a wearing posture of the user is incorrect, and the user is prompted for correct wearing, to improve wearing experience, and improve accuracy of detecting a heart rate, saturation of blood oxygen, and the like.

Still refer to FIG. 7. The smartwatch further includes a capacitive sensor 750. The capacitive sensor 750 may be designed into two symmetric rings as shown in FIG. 7, or may be designed into a single ring, a rectangle, or another shape. A function of the capacitive sensor 750 is the same as the function of the capacitive sensor 450 shown in FIG. 4. Details are not described herein again.

In some embodiments, a quantity of the second optical sensors 740 may be greater than or equal to 4, for example, may be 5 or 6, provided that information about light from the second optical transmitter 730 can be detected in all the four directions of up, down, left, and right. Such a quantity setting ensures accurate detection of a comfortably-worn state, and avoids false status determining due to swaying or the like. As shown in FIG. 8A, in the comfortably-worn state (the back side of the watch face corresponding to the PPG module clings to, that is, in direct contact with, skin), the back side of the watch face on which the optical transmitter and the optical sensors are mounted is parallel to skin 500 of the user, and a distance between the first optical transmitters 710 and the skin 500 is d1. The distance d1 may include a thickness of the PPG sensor module, or an overall thickness covering a translucent lens added to the PPG sensor module. FIG. 8A further shows a distance d2 between the second optical sensors 740 and the second optical transmitter 730. A field of view of the second optical transmitter 730 is FOV. A relationship between d2 and d1 is d2=d1×tan(FOV/2). For example, in the comfortably-worn state, the distance d1 between the first optical transmitters 710 and the skin 500 is 1.45 mm, the field of view FOV of the second optical transmitter 730 is 17°, and a wavelength is 850 nm. In this case, d2=0.22 mm. It can be learned that the second optical sensors 740 are very close to the second optical transmitter 730, and a structure of a component formed with the second optical transmitter 730 and the second optical sensors 740 is compact. When the PPG module is reused, a volume of the wearable device is not increased, and the wearable device is kept lightweight and thin.

A quantity of the first optical sensors 720 mainly depends on a requirement on accuracy in a solution with detection of physiological data, for example, a heart rate and saturation of blood oxygen. To fully cover detection of laser light leaked from the four directions of up, down, left, and right, four first optical sensors may be disposed in the directions of up, down, left, and right as shown in FIG. 4. It can be understood that, to more accurately detect laser light leaked from each direction, more first optical sensors may be further disposed. As shown in FIG. 7, eight first optical sensors may be disposed. Therefore, in this embodiment of this application, to further detect light transmitted by the VCSEL in a loosely-worn state, the quantity of the first optical sensors 720 is greater than or equal to 4, and may be 4 or 8 according to, for example, the embodiments shown in FIG. 4 and FIG. 7.

Figure 9:
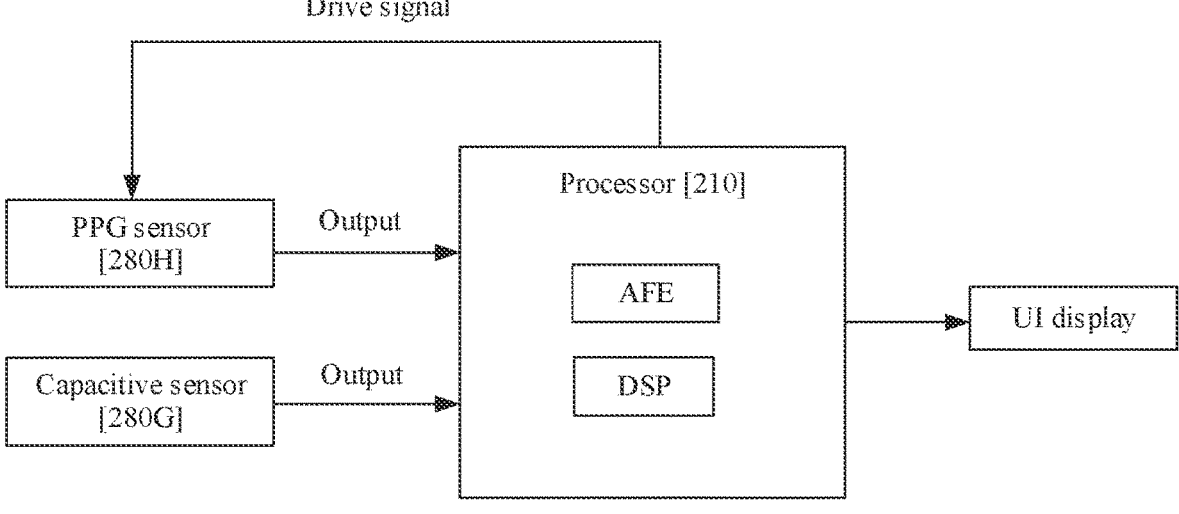
FIG. 9 is a schematic diagram of an architecture of a wearing status detection system in the wristband shown in FIG. 2.
Figure 10:
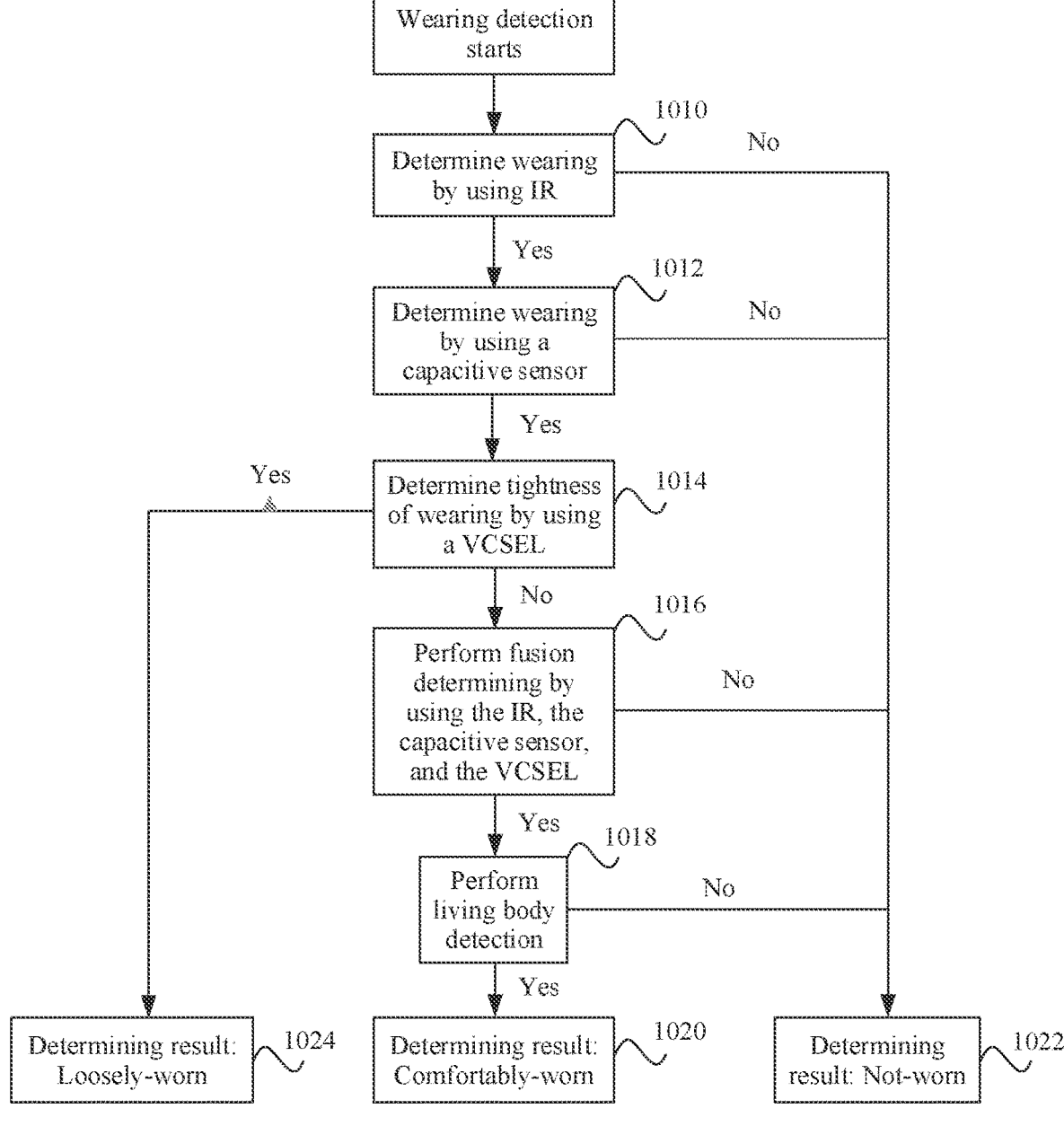
FIG. 10 is a schematic flowchart of a wearing status detection method according to an embodiment of this application.

With reference to FIG. 9 and FIG. 10, a wearing status detection method and a procedure related to this embodiment of this application are further described below.

FIG. 9 is a schematic diagram of an architecture of a wearing status detection system in the wristband shown in FIG. 2. FIG. 10 is a schematic flowchart of a wearing status detection method according to an embodiment of this application. The wearing status detection method may be applied to a wearable device having a structure including optical transmitters, optical sensors, and a capacitive sensor as arranged in FIG. 4 or FIG. 7. The wearable device has the architecture of the wearing status detection system as shown in FIG. 9. Refer to FIG. 10. The method specifically includes the following steps.

S1010: Wearing is determined by detecting reflectivity of IR light.

In some embodiments, the IR light may be transmitted by reusing an optical transmitter in a PPG module, for example, the first optical transmitter 410 including the infrared LED 413 shown in FIG. 4, or the first optical transmitters 710 including the infrared LEDs shown in FIG. 7. The infrared LEDs are in a normally-open state, and acquire a reflected signal of infrared light at preset time intervals. When there is something in front of the infrared LEDs, light reflectivity increases. With reference to FIG. 9, it can be learned that the PPG sensor 280H receives a drive signal transmitted by the processor 210, and drives an infrared LED to transmit light. After being reflected by skin, the infrared light is received by an optical sensor, for example, a photodiode, and the reflected infrared light signal is input to the processor 210. The processor 210 performs processing, for example, signal amplification and analog-to-digital conversion, by using an analog front end (Analog Front End, AFE). The DSP then performs processing and calculation of reflectivity of the infrared light according to a related algorithm, to determine whether a user has worn the wearable device. If a determining result obtained by the calculation of the processor is yes, that is, it is determined, through infrared light detection, that the wearable device is in a worn state, step S1012 is further performed. If a determining result by the calculation of the processor is no, that is, it is determined, by using IR, that the wearable device is not currently worn by the user, step S1022 is performed, and a determining result "Not worn" is output. Optionally, prompt information "Not worn" is displayed in a user interface (User Interface, UI) on a display screen of the wearable device.

It can be understood that the IR light may be transmitted not by reusing the optical transmitter in the PPG module, but by reusing an infrared light transmitter and an infrared light sensor that are disposed as independent in the wearable device, provided that a change of infrared light reflectivity can be detected.

S1012: Wearing is determined by using a capacitive sensor.

In some embodiments, a capacitive sensor is configured to measure a change of a capacitance value when the wearable device contacts the user. The capacitive sensor may be the capacitive sensor 450 shown in FIG. 4, or the capacitive sensor 750 shown in FIG. 7. The capacitive sensor is in a normally-open state. With reference to FIG. 9, it can be learned that the capacitive sensor 280G acquires a capacitance signal based on a preset sampling frequency, and transmits the detected capacitance signal to the processor. The processor uses a preset capacitance value or capacitance value range as a criterion for determining whether the wearable device is in the worn state. If a determining result of the processor is yes, that is, it is determined, through capacitance detection, that the wearable device is in a worn state, step S1014 is further performed. If a determining result of the processor is no, that is, it is determined, based on a capacitance, that the wearable device is not currently worn by the user, step S1022 is performed, and a determining result "Not worn" is output. Optionally, prompt information "Not worn" is displayed in the user interface (User Interface, UI) on the display screen of the wearable device.

S1014: Tightness of wearing is determined by using a VCSEL.

Specifically, when it indicates that the user has worn the wearable device after step S1012 and step S1014 are performed, that is, based on the IR reflection feature and the capacitance value, the processor transmits a drive signal to enable the PPG module, for example, the second optical transmitter 430, the second optical sensors 440, and the first optical sensors 420 that are shown in FIG. 4, or the second optical transmitter 730, the second optical sensors 740, and the first optical sensors 720 that are shown in FIG. 7. The second optical transmitter is a light-emitting component VCSEL. With reference to FIG. 9, it can be learned that the PPG sensor 280H transmits laser light after being enabled, detects light current signals in the first optical sensors and the second optical sensors, and transmits the light current signals to the processor. After the light current signals are processed by the AFE and calculated by the DSP, a quantity of first optical sensors that have received the laser light and a quantity of second optical sensors that have received the laser light may be determined. The processor determines the tightness of wearing based on the quantities of first optical sensors and second optical sensors that have received the laser light, that is, determines a wearing status of the wearable device. If a determining result obtained by the calculation of the processor is yes, that is, it is determined, through VCSEL detection, that the wearable device is in a loosely-worn state, step S1024 is further performed. If a determining result by the calculation of the processor is no, that is, it is determined, through VCSEL detection, that the wearable device is not in a loosely-worn state, step S1016 is performed.

The wearing status of the wearable device may be set to including a plurality of cases based on an actual requirement. For example, the wearing status includes at least loosely-worn and comfortably-worn. When the quantity of second optical sensors that have received the laser light is greater than or equal to 1, and the quantity of first optical sensors that have received the laser light is greater than or equal to 1, the wearing status of the wearable device is loosely-worn; or when the quantity of second optical sensors that have received the laser light is greater than or equal to 2, and the quantity of first optical sensors that have received the laser light is 0, the wearing status of the wearable device is comfortably-worn. In another example, an algorithm threshold for comfortably-worn may be lower. When the quantity of second optical sensors that have received the laser light is greater than or equal to 1, and the quantity of first sensors that have received the laser light is 0, the wearing status of the wearable device is comfortably-worn. Optionally, the wearing status may further include tightly-worn, not-worn, worn, and the like. Alternatively, the wearing status may further include correctly-worn, incorrectly-worn, and the like.

One or more of the foregoing steps S1010, S1012, and S1014 may be performed, and a sequence of executing the steps may further be correspondingly changed. For example, steps S1010 and S1012 may not be performed. The wearing status can alternatively be determined based on only the VCSEL, and a plurality of wearing states such as worn, not-worn, loosely-worn, and comfortably-worn are included. For another example, S1014 may be performed after only step S1010 is performed, or step S1010 may not be performed, and S1014 is performed after only step S1012 is performed. In other words, in the wearing status detection method provided in this embodiment of this application, the tightness of wearing may be determined based on the VCSEL with the IR wearing detection as a basis, or a determining result may be obtained based on wearing detection of the capacitive sensor and determining of the tightness of wearing by using the VCSEL. Clearly, compared with a case in which an infrared LED in the PPG module is first reused to detect the worn or not-worn state, and the VCSEL is then used to determine the tightness of wearing, simply enabling the light-emitting element VCSEL to detect all wearing states requires higher power consumption, but a detection result is more accurate.

S1016: Fusion determining is performed based on results of wearing determining by using the IR, the capacitive sensor, and the VCSEL.

In this embodiment of this application, based on step S1010, step 1012, and step 1014, the processor may further determine, by using a fusion algorithm, the wearing status of the wearable device based on the results of wearing determining in the foregoing steps. For example, different weighting coefficients may be set for the detected VCSEL reflection feature, IR light reflectivity, and contact capacitance, and the wearing status is finally determined by multiplying each of the three detection results by a weighting coefficient corresponding to the result. If a result of the fusion determining performed by the processor is yes, that is, it is determined, based on the detection results by using the IR, the capacitive sensor, and the VCSEL, that the wearable device is in the worn state, step S1018 is performed. If a result of the fusion determining performed by the processor is no, that is, the wearable device is not currently worn by the user, step S1022 is performed, and a determining result "Not worn" is output.

S1018: Living body detection is performed.

In this embodiment of this application, living body detection may be further performed when the result of the fusion determining performed by the processor in step S1016 is yes, to ensure that it is the user who is wearing the wearable device. For example, green light is transmitted by reusing the optical transmitter in the PPG module, and the green light is partially absorbed on a substance. Whether the substance is a living body can be determined by using the optical sensor to detect the reflected green light. Specifically, a reflected optical signal detected by the optical sensor may be processed to obtain a direct current (DC) component and an alternating current (AC) component. If the direct current (DC) component and/or the alternating current (AC) component are within preset ranges, it may be determined that the substance is a living body, that is, a living body detection result is yes. If the obtained direct current (DC) component and/or the alternating current (AC) component are not within preset ranges, it may be determined that the substance is not a living body, that is, the living body detection result is no. If the living body detection result is yes, step S1020 is performed. If the living body detection result is no, step S1022 is performed.

It can be understood that step S1018 is an optional and additional step for further improving accuracy of wearing detection.

S1020: The processor determines that the current wearing status is comfortably-worn.

If the living body detection result in step S1018 is yes, the processor determines, based on one or more detection results in S1010, S1012, S1014, S1016, and S1018, the current wearing status of the wearable device, and obtains the determining result, that is, comfortably-worn.

S1022: The processor determines that the current wearing status is not-worn.

If the result of wearing determining by using the IR in step S1010 is no, the result of wearing determining by using the capacitive sensor in step S1012 is no, the result of fusion determining based on the results of wearing determining by using the IR, the capacitive sensor, and the VCSEL in step S1016 is no, or the living body detection result in step 1018 is no, the processor determines, based on one or more detection results in S1010, S1012. S1016, and S1018, the current wearing status of the wearable device, and obtains the determining result, that is, not-worn.

S1024: The processor determines that the current wearing status is loosely-worn.

If the result of determining of the tightness of wearing by using the VCSEL in step S1014 is yes, the processor determines, based on the determining result, that a result of determining the current wearing status of the wearable device is loosely-worn.

In some embodiments, the processor may output the determining results obtained in S1020 to S1024 to the display screen, and a user may learn about the current wearing status by viewing the display screen. An example in which the wearing status includes three states, that is, not-worn, comfortably-worn, and loosely-worn is used for description below.

Figure 11A:
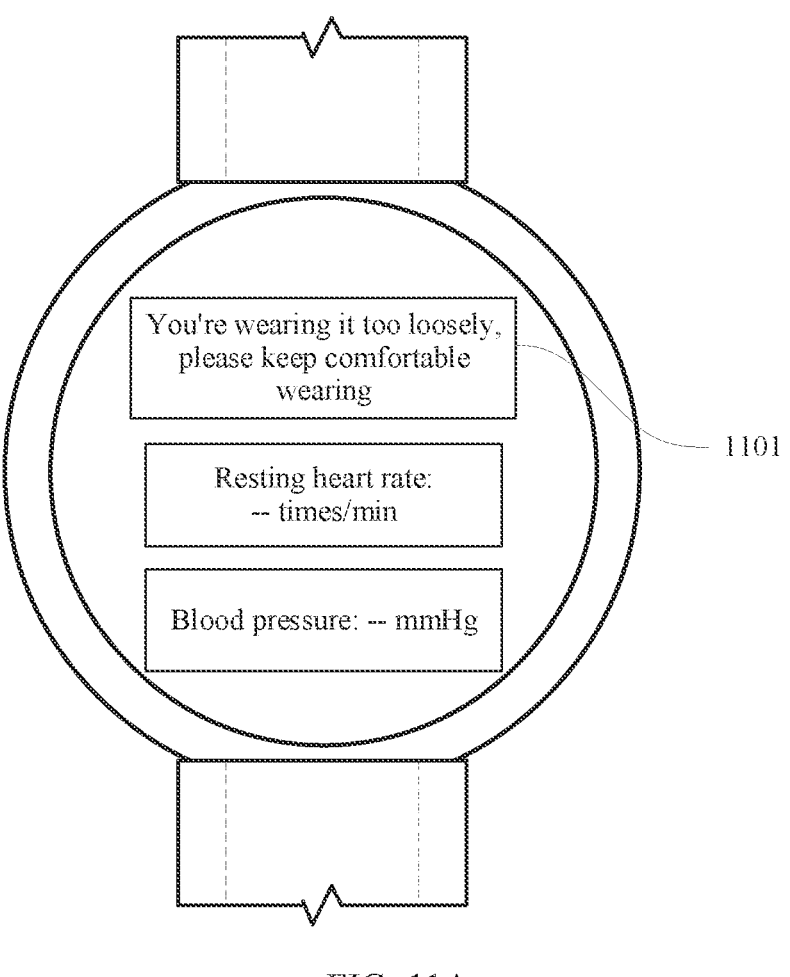
FIG. 11A and FIG. 11B are schematic diagrams of a set of interfaces on the smartwatch shown in FIG. 3.

After the wearing status of the wearable device is determined, a prompt may be generated when the wearing status is not normal. The prompt may be provided in a form of an image or text. For example, information that the wearing status does not conform to a standard is provided as a system notification or in an interface of an application for, for example, heart rate measurement or motion measurement. For example, as shown in FIG. 11A, when wearing is in a state that is too loose, the wearing status as textual information 1101 "You're wearing it too loosely, please keep comfortable wearing" may be displayed on the display screen of the wearable device. Further, according to a received instruction of a user, a video or an image and text for guidance on correct wearing may be further displayed. Alternatively, when the status of the wristband does not conform to the standard, a vibration prompt may be provided. For example, the vibration prompt is provided by using a buzzer. Alternatively, when the status of the wristband does not conform to the standard, a voice prompt may be provided. For example, the voice prompt is provided by using a loudspeaker. Optionally, because wearing is currently too loose, and the user has not kept wearing the device comfortably, the wearable device does not measure a heart rate or a blood pressure, and therefore a detected value of physiological data is not displayed.

Figure 11B:
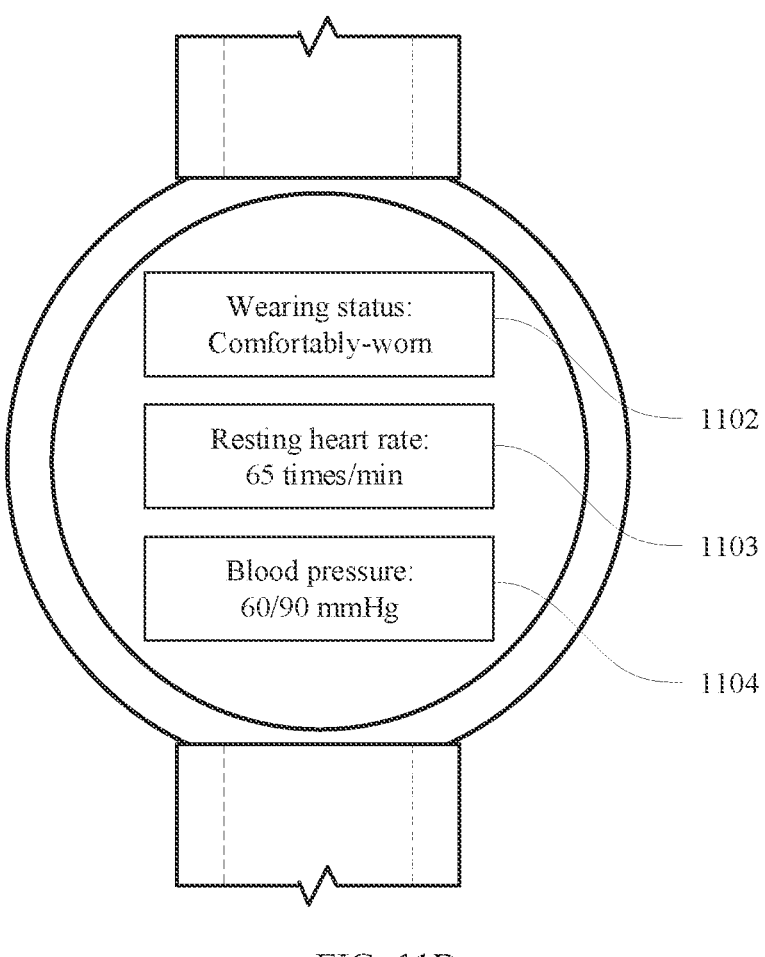

After the wearing status of the wearable device is determined, when the wearing status is normal, physiological data, for example, a heart rate, a blood pressure, saturation of blood oxygen, and an electrocardiogram may be directly detected, and the wearing status and a detection value of a physiological parameter are displayed on the display screen of the wearable device. A prompt may be provided in a form of an image or text. For example, the wearing status that conforms to the standard and the physiological detection value is provided as a system notification or in an interface of an application for, for example, heart rate measurement or motion measurement. For example, as shown in FIG. 11B, when the wearing status is normal, the wearing status as textual information 1102 "Wearing status: Comfortably-worn", and the detected physiological data value 1103 "Resting heart rate: 65 times/min" and 1104 "Blood pressure: 60/90 mmHg" may be displayed on the display screen of the wearable device. Alternatively, when the status of the wearable device conforms to the standard, a vibration prompt may be provided. For example, the vibration prompt is provided by using a buzzer. Alternatively, when the status of the wearable device conforms to the standard, a voice prompt may be provided. For example, the voice prompt is provided by using a loudspeaker.

All or some of the foregoing embodiments of the present invention may be implemented by using software, hardware, firmware, or any combination thereof. When software is used for implementation, all or some embodiments may be implemented in a form of a computer program product. The computer program product includes one or more computer instructions. When the computer program instruction is loaded and executed on a computer, the procedures or functions according to embodiments of the present invention are all or partially generated. The computer may be a general-purpose computer, a dedicated computer, a computer network, or another programmable apparatus. The computer instruction may be stored in a computer-readable storage medium or may be transmitted from a computer-readable medium to another computer-readable medium. For example, the computer instruction may be transmitted from a website, computer, server, or data center to another website, computer, server, or data center in a wired (for example, using a coaxial cable, an optical fiber, or a digital subscriber line (digital subscriber line, DSL)) or wireless (for example, via infrared, radio, or microwaves) manner. The computer-readable storage medium may be any usable medium accessible by the computer, or a data storage device, for example, a server or a data center, integrating one or more usable media. The usable medium may be a magnetic medium (for example, a floppy disk, a hard disk, or a magnetic tape), an optical medium (for example, a DVD), a semiconductor medium (for example, a solid-state drive), or the like.

The foregoing descriptions are merely example specific implementations of this application, but are not intended to limit the protection scope of this application. Any variation or replacement readily figured out by a person skilled in the art within the technical scope disclosed in this application shall fall within the protection scope of this application. Therefore, the protection scope of this application shall be subject to the protection scope of the claims.

What is claimed is:

1. A wearable device, comprising:
a first optical transmitter configured to transmit first optical signals;
one or more first optical sensors configured to detect the first optical signals;
a second optical transmitter, wherein the second optical transmitter is a vertical-cavity surface-emitting laser configured to transmit laser light, and wherein the second optical transmitter has a smaller field of view than the first optical transmitter;
one or more second optical sensors configured to detect the laser light from the second optical transmitter; and
one or more processors connected to the first optical transmitter, the one or more first optical sensors, the second optical transmitter, and the one or more second optical sensors are configured to determine and output a wearing status output of the wearable device based on a combination of the first optical signals detected by the first optical sensors and the smaller field of view of the laser light detected by the second optical sensors.

2. The wearable device of claim 1, wherein the one or more second optical sensors comprises at least four second optical sensors evenly disposed around the second optical transmitter, and wherein the at least four second optical sensors are disposed between the second optical transmitter and the one or more first optical sensors.

3. The wearable device of claim 2, wherein the one or more first optical sensors comprise four first optical sensors disposed in a one-to-one correspondence with four of the at least four second optical sensors.

4. The wearable device of claim 1, wherein the one or more first optical sensors comprise eight first optical sensors, wherein the one or more second optical sensors comprise four second optical sensors, wherein the eight first optical sensors are evenly disposed around the second optical transmitter and the four second optical sensors, and wherein four of the first optical sensors are disposed in a one-to-one correspondence with the four second optical sensors.

5. The wearable device of claim 1, wherein when the first optical sensors have not detected laser light and the one or more second optical sensors have detected laser light, the one or more processors are configured to determine that the wearing status is comfortably-worn, and wherein when the one or more first optical sensors have detected the laser light and the one or more second optical sensors have detected the laser light, the one or more processors are configured to determine that the wearing status is loosely-worn.

6. The wearable device of claim 1, wherein when the first optical sensors have not detected laser light and two or more second optical sensors have detected laser light, the one or more processors are configured to determine that the wearing status is comfortably-worn, and wherein when the one or more first optical sensors have detected laser light and the one or more second optical sensors have detected the laser light, the one or more processors are configured to determine that the wearing status is loosely-worn.

7. The wearable device of claim 1, wherein the wearable device further comprises a display screen configured to display the wearing status output.

8. The wearable device of claim 1, wherein the wearable device further comprises a prompt component configured to prompt a user when the wearing status is loosely-worn.

9. The wearable device of claim 1, wherein the wearable device comprises a capacitive sensor configured to detect contact capacitance and transmit a detected capacitance value to the one or more processors, and wherein the one or more processors are configured to determine the wearing status of the wearable device based on the first optical signals detected by the one or more first optical sensors and the one or more second optical sensors and based on the detected capacitance value.

10. The wearable device of claim 9, wherein the first optical transmitter is configured to transmit an infrared light, wherein a third optical sensor of the one or more first optical sensors is configured to detect the infrared light and to transmit a detected infrared light signal to the one or more processors, and wherein the one or more processors are configured to determine the wearing status of the wearable device based on optical signals detected by the one or more first optical sensors and the one or more second optical sensors, the detected infrared light signal, and the detected capacitance value.

11. The wearable device of claim 1, wherein the first optical transmitter, the one or more first optical sensors, and the second optical transmitter are photoplethysmography (PPG) apparatus components, and wherein the second optical transmitter is in a center of the PPG apparatus.

12. The wearable device of claim 1, further comprising a shading wall disposed between the first optical transmitter and the one or more first optical sensors, between the second optical transmitter and the one or more second optical sensors, or between the one or more second optical sensors and the first optical transmitter.

13. A method comprising:
   transmitting, by a first optical transmitter, first optical signals;
   transmitting, by a second optical transmitter, laser light, wherein the second optical transmitter is a vertical-cavity surface-emitting laser, wherein the second optical transmitter has a smaller field of view than the first optical transmitter;
   performing first detection, by one or more first optical sensors, of the first optical signals;
   performing second detection, by one or more second optical sensors, of reflected laser light transmitted by the second optical transmitter; and
   outputting, based on a combination of the first optical signals from the first detection and the smaller field of view of the laser light from the second detection, a wearing status output of a wearable device.

14. The method of claim 13, wherein before transmitting, by the second optical transmitter, the laser light, the method further comprises:
   transmitting, by the first optical transmitter, infrared light;
   detecting, by the one or more first optical sensors, infrared light;
   determining, based on detected infrared light, the wearing status;
   transmitting, by the second optical transmitter, the laser light when the wearing status is worn;
   detecting, by the one or more first optical sensors and the one or more second optical sensors, reflected laser light; and further
   determining, based on the reflected laser light, the wearing status.

15. The method of claim 13, wherein the wearable device comprises a capacitive sensor configured to detect contact capacitance, and wherein before the transmitting by the second optical transmitter, the method further comprises:

determining, based on the contact capacitance, the wearing status;
   transmitting, by the second optical transmitter, the laser light when the wearing status is worn;
   detecting, by the one or more first optical sensors and the one or more second optical sensors, reflected laser light; and
   determining, based on detected reflected laser light, the wearing status.

16. The method of claim 13, wherein determining the wearing status based on the laser light detected by the one or more first optical sensors and the one or more second optical sensors comprises:
   determining that the wearing status of the wearable device is comfortably-worn when the first optical sensors have not detected laser light and the one or more second optical sensors have detected laser light; and
   determining that the wearing status of the wearable device is loosely-worn when the one or more first optical sensors have detected the laser light and the one or more second optical sensors have detected the laser light.

17. The method of claim 13, wherein determining the wearing status of the wearable device based on the laser light detected by the one or more of the first optical sensors and the one or more second optical sensors comprises:
   determining that the wearing status of the wearable device is comfortably-worn when the one or more first optical sensors have detected no laser light and two or more second optical sensors have detected laser light; and
   determining that the wearing status of the wearable device is loosely-worn when the one or more of the first optical sensors have detected the laser light and the one or more second optical sensors have detected the laser light.

18. The method of claim 15, wherein determining the wearing status of the wearable device further comprises:
   determining the wearing status based on a first quantity of the first optical sensors that detect the laser light and a second quantity of the one or more second optical sensors that detect the laser light; and
   when the wearing status of the wearable device is a status other than loosely-worn, further determining the wearing status based on infrared light detected by the one or more first optical sensors, the contact capacitance, the first quantity of the first optical sensors that detect the laser light, and the second quantity of the one or more second optical sensors that detect the laser light.

19. A computer program product, comprising computer-executable instructions for storage on a non-transitory computer-readable medium that, when executed by one or more processors, cause a wearable apparatus to:
   transmit at least one light;
   transmit laser light at a smaller field of view than the least one light;
   detect at least the one light to obtain detected light;
   detect laser light to obtain detected laser light; and
   output, based on a combination of the detected light and the detected laser light corresponding to the smaller field of view, a wearing status of the wearable apparatus.

20. The computer program product of claim 19, wherein the computer-executable instructions further cause the wearable apparatus to:
   transmit infrared light;
   detect infrared light to obtain detected infrared light;

determine based on the detected infrared light, the wearing status;

transmit the laser light when the wearing status is worn;

detect reflected laser light; and further determine, based on the reflected laser light, the wearing status.

\* \* \* \* \*